(12) United States Patent
Potrawa et al.

(10) Patent No.: US 7,740,693 B2
(45) Date of Patent: Jun. 22, 2010

(54) ORGANIC FLUORESCENT SULFONYL UREIDO BENZOXAZINONE PIGMENTS

(75) Inventors: Thomas Potrawa, Seelze (DE); Joachim Schulz, Pohle (DE)

(73) Assignee: Honeywell International Inc.

( * ) Notice: Subject to any disclaimer, the term of this patent is extended or adjusted under 35 U.S.C. 154(b) by 476 days.

(21) Appl. No.: 11/906,289

(22) Filed: Oct. 1, 2007

(65) Prior Publication Data

US 2009/0085344 A1 Apr. 2, 2009

(51) Int. Cl.
- C09D 11/00 (2006.01)
- C09K 11/06 (2006.01)
- C07D 265/14 (2006.01)
- C08K 5/1545 (2006.01)
- B05D 1/00 (2006.01)
- B42D 15/10 (2006.01)
- D21H 21/40 (2006.01)

(52) U.S. Cl. .............. 106/31.15; 252/301.16; 252/301.34; 252/301.35; 544/92; 524/87; 427/466; 283/92; 162/158

(58) Field of Classification Search .......... 106/31.15, 106/31.77; 544/92; 252/301.16, 301.34, 252/301.35; 524/87; 427/466; 283/92; 162/158
See application file for complete search history.

(56) References Cited

U.S. PATENT DOCUMENTS

| 3,740,402 | A | * | 6/1973 | Cevasco ............ 544/92 |
| 3,892,972 | A | * | 7/1975 | Cevasco ............ 252/301.16 |
| 5,871,854 | A | * | 2/1999 | Tokida et al. ........ 428/690 |
| 6,743,283 | B2 | | 6/2004 | Imanishi et al. ....... 106/31.14 |
| 7,192,471 | B2 | * | 3/2007 | Potrawa et al. ........ 106/31.15 |
| 7,205,296 | B2 | * | 4/2007 | Scarborough et al. ... 544/92 |
| 2006/0065154 | A1 | | 3/2006 | Potrawa et al. ........ 106/31.15 |
| 2006/0069093 | A1 | | 3/2006 | Scarborough et al. |

FOREIGN PATENT DOCUMENTS

EP 0 314 350 5/1989

OTHER PUBLICATIONS

Structure activity relationships of novel antibacterial trnslation inhibitors, Jamie M. Froelich, et al., Bioorganic & Medicinial Chemistry Letters, Aug. 2006, vol. 16, pp. 5451-5456.

* cited by examiner

Primary Examiner—Helene Klemanski

(57) ABSTRACT

The present disclosure provides Benzoxazinone compounds represented by the formula:

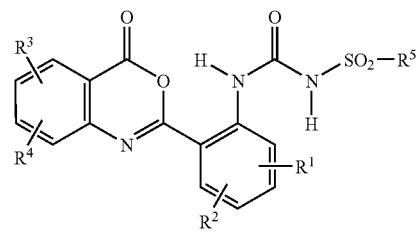

wherein each $R^1$, $R^2$, $R^3$, and $R^4$ is independently selected from hydrogen, alkyl of 1-12 carbon atoms, substituted alkyl, aryl of 6-12 carbon atoms, substituted aryl, halo, and alkoxy; and $R^5$ is selected from alkyl of 1-12 carbon atoms, substituted alkyl, aryl of 6-12 carbon atoms, substituted aryl, halo, and alkoxy; wherein each of the substituted alkyl and the substituted aryl groups have a substituent selected from alkyl, aryl, halo, and alkoxy. The present disclosure provides a mark having a benzoxazinone compound, and a method for applying the mark onto an article. Also provided is a process for preparing benzoxazinone compounds.

16 Claims, 1 Drawing Sheet

ORGANIC FLUORESCENT SULFONYL UREIDO BENZOXAZINONE PIGMENTS

BACKGROUND OF THE INVENTION

1. Field of the Invention

The present disclosure relates to fluorescent sulfonyl ureido benzoxazinone pigments and a process for preparing the same. More particularly, the present disclosure relates to fluorescent sulfonyl ureido benzoxazinone pigments that are colorless. The benzoxazinone pigments may be used in ink compositions in a wide variety of printing systems, such as inkjet printing systems, and are particularly well-suited for security applications.

2. Description of the Related Art

Fluorescent pigments emitting in the yellow-green region are well known. However, for many applications, such as security-related applications, colorless pigments, which fluoresce in the visible region, are needed. For instance, some well-known fluorescent pigments, such as fluorescein, rhodamine, and coumarin, have an appearance and color under normal lighting conditions that are not desirable for certain security applications and printing systems. Another desirable characteristic of fluorescent pigments is to maintain lightfastness over a length of time after their application to a substrate.

Benzoxazinone compounds are colorless, fluorescent pigments that are the state of the art. See, e.g., EP 0 314 350. However, the preparation of these compounds involves a multi-step synthesis or a one-step process that generates a large amount of non-environmentally friendly waste. For example, benzoxazinone compounds may be prepared by reacting an aromatic sulfonyl chloride with anthranilic acid in pyridine as solvent and as base; however, during the work up, water is added and the pyridine reactant cannot be recycled easily, producing non-environmentally friendly waste. In addition, purification by column chromatography or recrystallization with methylene chloride is often necessary with this process, producing an additional source of non-environmentally friendly waste. Therefore, a need exists in the art for more colorless compounds that brightly fluoresce in certain emission wavelengths under UV irradiation, and a process for preparing such compounds that is commercially practical and environmentally friendly.

SUMMARY OF THE INVENTION

The present disclosure provides sulfonyl ureido benzoxazinone compounds represented by the formula:

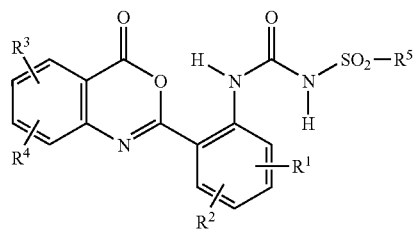

wherein each $R^1$, $R^2$, $R^3$, and $R^4$ is independently selected from hydrogen, alkyl of 1-12 carbon atoms, substituted alkyl, aryl of 6-12 carbon atoms, substituted aryl, halo, and alkoxy; and $R^5$ is selected from alkyl of 1-12 carbon atoms, substituted alkyl, aryl of 6-12 carbon atoms, substituted aryl, halo, and alkoxy; and wherein each of the substituted alkyl and the substituted aryl groups have a substituent selected from alkyl, aryl, halo, and alkoxy.

The present disclosure also provides a process for preparing sulfonyl ureido benzoxazinone compounds represented by the formula:

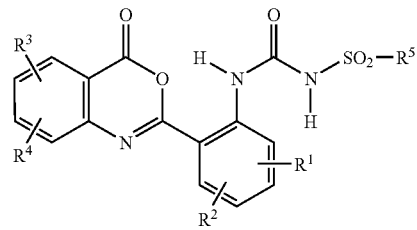

wherein each $R^1$, $R^2$, $R^3$, $R^4$ and $R^5$ is as defined above; where the process includes the steps of contacting:

(i) an anthranilic acid derivative represented by the formula:

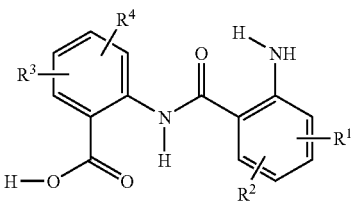

wherein each $R^1$, $R^2$, $R^3$, and $R^4$ is independently selected from hydrogen, alkyl of 1-12 carbon atoms, substituted alkyl, aryl of 6-12 carbon atoms, substituted aryl, halo, and alkoxy, wherein each of the substituted alkyl and the substituted aryl groups have a substituent selected from alkyl, aryl, halo, and alkoxy; and (ii) a sulfonyl isocyanate represented by the formula:

wherein $R^5$ is selected from alkyl of 1-12 carbon atoms, substituted alkyl, aryl of 6-12 carbon atoms, substituted aryl, halo, and alkoxy; wherein each of the substituted alkyl and the substituted aryl groups have a substituent selected from alkyl, aryl, halo, and alkoxy; and wherein the contacting step is carried out optionally in the presence of a solvent and/or a catalyst at a temperature and length of time sufficient to produce a sulfonylurea derivative represented by the formula:

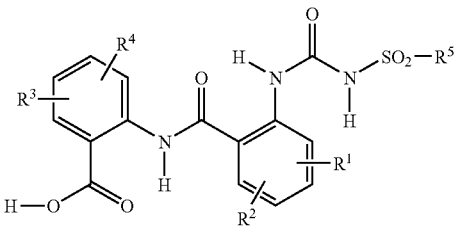

and thereafter dehydrating the sulfonylurea derivative under conditions sufficient to produce a sulfonyl ureido benzoxazinone compound. In this process, only one ketone (such as methyl ethyl ketone) is used as solvent, and acetic acid anhydride is used for ring closure. Because this process uses an isocyanate derivative and employs chemical addition, no acids or bases are generated or needed, thereby avoiding the undesirable use of pyridine and eliminating the need for further purification steps.

The present disclosure also provides a mark comprising the benzoxazinone compositions of the present disclosure. The mark may be applied by printing on a substrate or an article.

The present disclosure also provides a method for applying a mark to an article, where the mark comprises the benzoxazinone compounds of the present disclosure. The method includes the step of printing a mark on an article or a substrate via at least one printing system, wherein the printing system is selected from the group consisting of ink jet printing, thermal inkjet printing, piezo printing, dot matrix printing, and/or laser printing.

The process of the present disclosure offers the advantages of producing the disclosed sulfonyl ureido benzoxazinone compounds in high yield and high purity, thereby providing a commercially-viable process, while avoiding the formation of by-products that would diminish the purity of the benzoxazinone compounds. The benzoxazinone compositions of the present disclosure are fluorine-free, and thereby are more environmentally friendly than compositions containing fluorine groups.

DETAILED DESCRIPTION OF THE INVENTION

Figure 1:
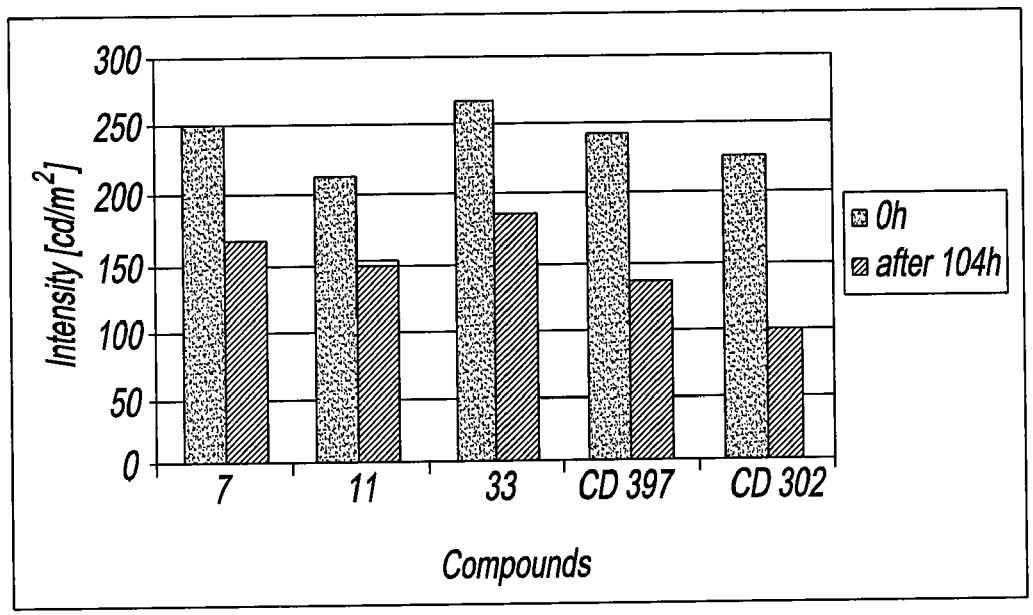
FIG. 1 is a comparative bar graph of the lightfastness of 1-(para-toluenesulfonyl)-3-[2-(4-oxo-4H-benzo[d]-[1,3]oxazine-2-yl)-phenyl]urea (compound 7), as compared with aliphatic ureidobenzoxazinone (UBO)(compound 11), Nitril-AUBO (compound 33), Lumilux® CD 397, and Lumilux® CD 302, by measuring relative intensities at 0 hours and after 104 hours.

The benzoxazinone compounds of the present disclosure are represented by the formula:

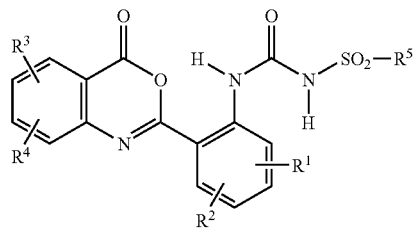

wherein each $R^1$, $R^2$, $R^3$, and $R^4$ is independently selected from hydrogen, alkyl of 1-12 carbon atoms, substituted alkyl, aryl of 6-12 carbon atoms, substituted aryl, halo, and alkoxy; and $R^5$ is selected from alkyl of 1-12 carbon atoms, substituted alkyl, aryl of 6-12 carbon atoms, substituted aryl, halo, and alkoxy; and wherein each of the substituted alkyl and the substituted aryl groups have a substituent selected from alkyl, aryl, halo, and alkoxy.

Preferably, $R^1$, $R^2$, $R^3$, and $R^4$ are each hydrogen; and $R^5$ is selected from alkyl of 1-12 carbon atoms, substituted alkyl, aryl of 6-12 carbon atoms, substituted aryl, halo, and alkoxy; wherein each of the substituted alkyl and the substituted aryl groups have a substituent selected from alkyl, aryl, halo, and alkoxy.

More preferably, each of $R^1$, $R^2$, $R^3$, and $R^4$ are hydrogen, and $R^5$ is selected from the group consisting of phenyl, 2-methylphenyl, 4-methylphenyl, and 4-chlorophenyl. An embodiment of a preferred compound is 1-(para-toluenesulfonyl)-3-[2-(4-oxo-4H-benzo[d][1,3]oxazine-2-yl)-phenyl]urea, also named 1-(4-methylphenylsulfonyl)-3-[2-(4-oxo-4H-benzo[d][1,3]oxazine-2-yl)-phenyl]urea.

The benzoxazinone compounds of the present disclosure are colorless, and fluoresce in the visible region. More specifically, the benzoxazinone compounds of the present disclosure produce a bright emission in a region from about 520 nm to about 540 nm wavelength when irradiated by UV light energy at about 366 nm wavelength. The benzoxazinone compounds have an excitation maximum at about 340 nm to about 420 nm wavelength.

The term "colorless," as used herein, indicates that a material does not absorb light or interact with light. The terms "nearly colorless" or "substantially colorless," which are used interchangeably herein, indicate that a material is devoid of significant absorption of light in the visible light spectrum (400-700 nm), and does not present a distinct hue in reflected or transmitted light in sunlight or in normal room lighting conditions. As used in this application, "colorless," "nearly colorless," and "substantially colorless" materials are all understood to include "white" materials. Typically, "colorless" is used to refer to a transparent material through which light passes without being absorbed (such as a crystal or solution), while "white" is used for a material where all the light is reflected (such as milk). The same material or compound can be both colorless and white. For example, a quartz crystal is colorless, and the powder of the same quartz crystal is white.

The present disclosure further provides a process for the preparation of benzoxazinone compounds represented by the formula:

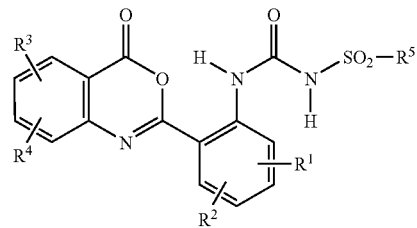

wherein the process for preparing includes the steps of contacting:

(i) an anthranilic acid derivative represented by the formula:

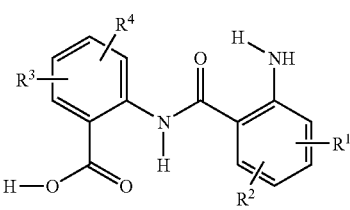

and
(ii) a sulfonyl isocyanate represented by the formula:

$$O=C=N-SO_2-R^5$$

wherein $R^1$, $R^2$, $R^3$, $R^4$ and $R^5$ are as previously defined; and thereafter dehydrating the urea derivative under conditions sufficient to produce the desired sulfonyl ureido benzoxazinone compounds of the present disclosure.

Preferably, the sulfonyl isocyanate used in the process of preparation is selected from the group consisting of phenylsulfonyl isocyanate, 2-methylphenylsulfonyl isocyanate, 4-methylphenylsulfonyl isocyanate, and 4-chlorophenylsulfonyl isocyanate. A preferred embodiment for the process includes using para-toluenesulfonyl isocyanate, where $R^1$, $R^2$, $R^3$, and $R^4$ are each hydrogen atoms and $R^5$ is a para-tolyl group, as the sulfonyl isocyanate to produce the benzoxazinone compound 1-(para-toluenesulfonyl)-3-[2-(4-oxo-4H-benzo[d][1,3]oxazine-2-yl)-phenyl]urea.

Preferably, the urea derivative is represented by the formula:

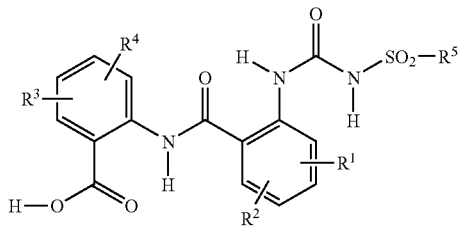

wherein $R^1$, $R^2$, $R^3$, $R^4$, and $R^5$ are as previously defined for the benzoxazinone compounds above.

Preferably, the step of dehydrating the urea derivative is carried out by heating the urea derivative at a temperature, and for a period of time, sufficient to produce the desired benzoxazinone compound.

Alternatively, the step of dehydrating the urea derivative is carried out by contacting the urea derivative and a dehydrating agent at a sufficient temperature, and for a sufficient period of time, to produce the desired benzoxazinone compounds.

The contacting step in the present disclosure is preferably carried out at a temperature from about 50° C. to about 90° C., at a pressure of about 1 atmosphere, and for a length of time from about 1 hours to about 8 hours. These reaction conditions are sufficient to effect dehydration of the sulfonylurea derivative to produce the sulfonyl ureido benzoxazinone compound.

More preferably, the contacting step in the present disclosure is carried out at a temperature from about 75° C. to about 85° C., and for a length of time from about 3 hours to about 5 hours.

The process for preparing the benzoxazinone compounds of the present disclosure can be performed either as a batch process or as a continuous process.

The reactor for the process can further include a diluent, which may be a solvent or a mixture of solvents, such as aliphatic ketones.

The process can further include one or more of the following steps:
(1) cooling to a sub-ambient temperature to precipitate the reaction product; and
(2) isolating the product from the reaction mixture in substantially pure form.

In practice, preferably at least 10 wt % of the reactants are converted to a benzoxazinone compound by this process. More preferably, up to at least 80 wt % of the reactants are converted to a benzoxazinone compound, and most preferably, at least 90 wt % of the reactants are converted to the benzoxazinone compound.

Referring now to the Figures, FIG. 1 illustrates a comparative bar graph of the intensity of lightfastness (in $cd/m^2$) of 1-(para-toluenesulfonyl)-3-[2-(4-oxo-4H-benzo[d]-[1,3]oxazine-2-yl)-phenyl]urea (compound 7), which is shown relative to various ureido benzoxazinone compounds (UBO), such as aliphatic UBO (compound 11), Nitril-AUBO (compound 33), and Lumilux® CD 397 and Lumilux® CD 302.

Benzoxazinone compounds Lumilux® CD 397 and Lumilux® CD 302 are commercially available, proprietary products of Honeywell under the Lumilux® CD brand name (Honeywell Specialty Chemicals, Seelze GmbH, Seelze, Germany). Compounds 11 and 33 are 1-(chloracetyl)-3-[2-(4-oxo-4H-benzo[d]-[1,3]oxazine-2-yl)-phenyl]urea and 1-(4-cyanophenyl)-3-[2-(4-oxo-4H-benzo[d]-[1,3]oxazine-2-yl)-phenyl]urea, respectively.

Figure 2:
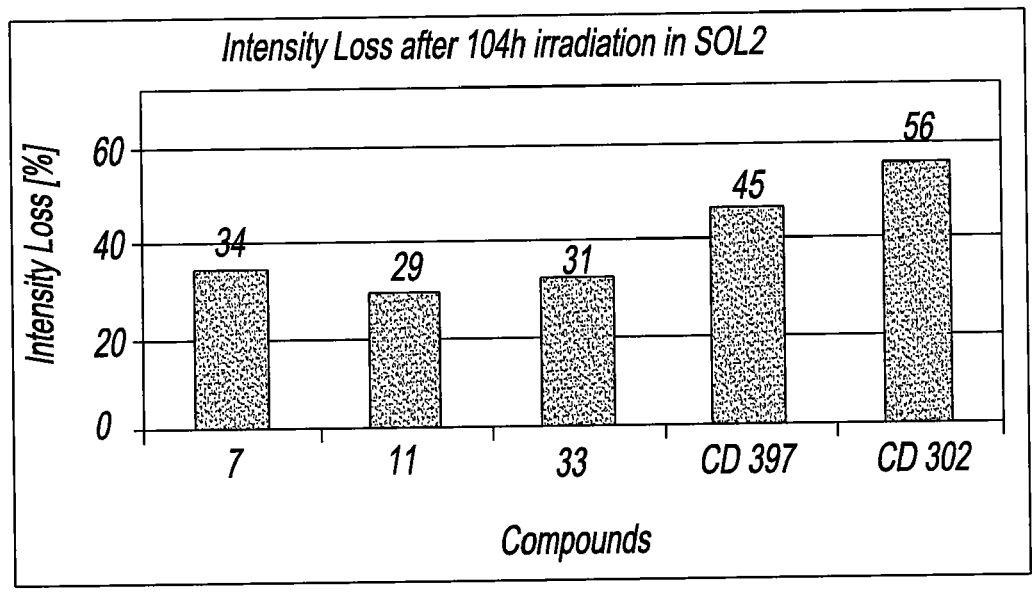
FIG. 2 is a comparative bar graph of the percent (%) loss of intensity of lightfastness of 1-(para-toluenesulfonyl)-3-[2-(4-oxo-4H-benzo[d]-[1,3]oxazine-2-yl)-phenyl]urea (compound 7) relative to compound 11, compound 33, Lumilux® CD 397, and Lumilux® CD 302.

FIG. 2 is a comparative bar graph illustrating of the percent loss of intensity of lightfastness of 1-(para-toluenesulfonyl)-3-[2-(4-oxo-4H-benzo[d]-[1,3]oxazine-2-yl)-phenyl]urea (compound 7) compared with ureido benzoxazinone compounds (UBO) such as compound 11, compound 33, Lumilux® CD 397 and Lumilux® CD 302.

It can be seen from FIGS. 1 and 2 that 1-(para-toluenesulfonyl)-3-[2-(4-oxo-4H-benzo[d]-[1,3]oxazine-2-yl)-phenyl]urea (7) has a greater degree (intensity) of lightfastness, and lower loss of lightfastness intensity, than either Lumilux® CD 397 and Lumilux® CD 302. Greater lightfastness and less loss of lightfastness intensity are advantages of the new product as compared with the state of the art materials.

Preferably, when the benzoxazinone compounds of the present disclosure are irradiated with an ultraviolet light source, the benzoxazinone compounds emit fluorescence in the visible spectrum, making these benzoxazinone compounds particularly useful as pigments for security applications, such as uses for security inks and fibers.

The present disclosure also provides a mark comprising the benzoxazinone compositions of the present disclosure. The marks may be applied by printing the mark or marks on a substrate, such as an article of commerce. The marks may be printed on an article of commerce that is at least one selected from the group consisting of currency, passports, chip cards, checks, check cards, credit cards, debit cards, identity cards, certificates, bank notes, and postal items.

The present disclosure further provides a method for applying a mark to an article by printing the mark on to the article. The mark is applied to an article or to a substrate via at least one printing system, wherein the printing system is selected from the group consisting of ink jet printing, thermal inkjet printing, piezo printing, dot matrix printing, laser printing, and combinations thereof.

While the range of emitted fluorescence for these benzoxazinone compounds varies from about 400 nm to about 585 nm wavelengths, the more preferred benzoxazinone compounds of the present disclosure exhibit a fluorescence maximum at 526 nm and an excitation maximum at 380 nm.

In addition, the compounds of this disclosure show a high degree of lightfastness that is particularly useful as an ultraviolet-type excitation fluorescent developer for ink compositions. This also makes the benzoxazinone compounds useful generally as pigments in security applications, and more particularly as pigments for use in security inks and fibers, fluorescent inks, colored paints, colorless paints, mass coloring polymers, films, coatings, and dispersions. The benzoxazinone compounds of the present disclosure also have utility as pigments used in data carriers, security markings, paper, spun fibers, dyed fibers, biochemistry tracers, and displays.

For example, ink compositions comprising benzoxazinone compounds of the present disclosure can be employed on a variety of indicia or data carrier substrates, including, but not limited to, currency, passports, chip cards, checks, check cards, credit cards, debit cards, identity cards, certificates, and bank notes.

Ink compositions of the present disclosure can be obtained by dissolving a benzoxazinone compound of the present disclosure in a suitable liquid medium. Suitable liquid media include at least one solvent. The solvent may be an inorganic solvent and/or an organic solvent. An example of an inorganic solvent is water. Examples of organic solvents include, but are not limited to, an aliphatic alcohol, ester or ketone solvent, and optionally mixing therewith one or more additional components usually contained in ink compositions, such as binder resins, surfactants, and the like. The benzoxazinone compound of the present disclosure is dissolved in the ink composition in any suitable amount, generally in an amount of from about 0.001% to about 30%, preferably from about 0.01% to about 3% by weight, based on the total weight of the ink composition. Preferably, the amount of the benzoxazinone compound should provide an acceptable amount of light emission sufficient to detect (i.e., read) the emission, either by the unaided human eye or by an electronic image device that is capable of detecting such fluorescence. However, using a very large amount of the benzoxazinone compound in the ink composition may cause a type of self-absorption resulting in reduction of emission intensity, and should be avoided. Typical examples for the preparation of ink compositions of this type are disclosed in U.S. Pat. No. 6,743,283 B2, which is incorporated herein by reference.

The solvent used to dissolve the benzoxazinone compounds of the present disclosure in the ink compositions may be water and/or at least one of any suitable organic solvent. A preferred organic solvent is an aliphatic alcohol solvent, which will minimize odor and adverse environmental effects. If the benzoxazinone compounds of the present disclosure are not sufficiently soluble in the aliphatic alcohol solvent, a mixture of the aliphatic alcohol solvent and another solvent, such as an ester (e.g., ethyl acetate) or a ketone (e.g., methylethylketone, methylisobutylketone and the like), may be employed.

For ink compositions requiring increased stability, or to prevent the ink from drying prematurely, the ink compositions of the present disclosure may include at least one high boiling point solvent, such as ethers (e.g., ethylene glycol monomethyl ether, ethylene glycol monoethyl ether, propylene glycol monomethylether), or aliphatic polyols (e.g., 1,2-hexanediol, 2,4,6-hexanetriol), and combinations thereof.

In the luminous ink composition of the preferred present disclosure, a binder resin is often included in order to fix the benzoxazinone compounds properly. The binder resin preferably has good solubility in the solvent, and the viscosity of the ink composition may be suitably adjusted when the binder resin is included in the ink composition. Specific examples of preferred binder resins include, but are not limited to: polyvinyl resins, such as polyvinyl alcohol, polyvinyl butyral, polyvinyl pyrrolidone, and vinyl pyrrolidone-vinyl acetate copolymers; polyamine resins such as polyallylamine, polyvinylamine and polyethyleneimine; polyacrylate resins such as polymethyl acrylate, polyethylene acrylate, polymethyl methacrylate and polyvinyl methacrylate; and amino resins, alkyd resins, epoxy resins, phenol resins, polyesterimide resins, polyamide resins, polyamideimide resins, silicone resins, phenol resins, ketone resins, rosin, rosin-modified resin phenols, maleic acid, fumaric acid resin, and the like; petroleum resins, cellulose resins such as ethyl cellulose and nitrocellulose; and natural resins such as gum arabic, gelatin, and the like.

Particularly preferred binder resins include polyvinyl resins, polyacrylate resins, and polyamine resins, which can be employed for ink compositions used for writing implements, inkjet printers, and printing.

"Ink" (or "inks"), as used herein, means a liquid substance or a dry powder containing pigments that can be used in printing systems to apply an image onto a surface or substrate. As used in the present disclosure, inks include, but are not limited to, liquid inks (such as those used by inkjet printers), as well as toners (such as those used by laser printers). Inkjet inks include, but are not limited to, water-based and solvent-based formulations.

The benzoxazinone compounds of the present disclosure may also be used as pigments in toners. Such toners may contain other materials to allow the toner to bind to a surface when heated. Toners may use resins, wax or similar materials as binders, and the formulation may also include release agents, charge control agents, and other additives. Such toners can be made by the conventional toner method or the chemically processed toner (CPT) method. Toner particles can be very small (one micron or smaller) so that the actual volume of a toner particle can be much smaller than the volume of inkjet ink released during the process of printing a single dot. The smallest discernable dot size with a laser type of printer can be adjusted to be smaller or larger, depending on the type of print system used.

The ink compositions comprising the benzoxazinone compounds of the present disclosure may be used in a wide variety of printing systems. The ink compositions of the present disclosure are well-suited for inkjet printing systems, preferably those systems using thermal inkjet technology, but also may be employed in inkjet printing systems using non-thermal technologies, such as those systems using piezo technology, and/or other ink delivery systems, such as dot matrix technology. The ink compositions of the present disclosure may also be used with toners and laser printing systems.

The ink compositions comprising the benzoxazinone compounds of the present disclosure offer the advantages of a high degree of lightfastness, invisibility in normal light to the unaided human eye or to electronic detection devices (such as barcode readers or digital camera lens) yet bright fluorescence upon irradiation with an ultraviolet light source, and high print quality and reliability.

The ink compositions comprising the benzoxazinone compounds of the present disclosure can be used to print images on a wide variety of substrates. The substrates that may be used in the present disclosure include, but are not limited to, paper, cloth, polymers/plastic films (such as polyester resins, polycarbonates and polyethylenes), metals, and glass. Paper substrates may be coated or uncoated, and the ink compositions are particularly useful for financial and security documents (e.g., checks, currency, stocks, bonds, passports, identity cards, and insurance papers).

The following non-limiting example is illustrative of the various embodiments of the present disclosure. It is within the ability of a person of ordinary skill in the art to select other variables from among the many known in the art without departing from the scope of the present disclosure. Accordingly, this example shall serve to further illustrate the present disclosure, not to limit it.

Experimental

Unless otherwise noted, all parts and percentages are on a weight basis.

EXAMPLE 1

Preparation of 1-(para-toluenesulfonyl)-3-[2-(4-oxo-4H-benzo[d]-[1,3]oxazine-2-yl)-phenyl]urea In accordance with the present disclosure, 1-(para-toluenesulfonyl)-3-[2-(4-oxo-4H-benzo[d][1,3]oxazine-2-yl)-phenyl]urea, also named 1-(4-methylphenylsulfonyl)-3-[2-(4-oxo-4H-benzo[d][1,3]oxazine-2-yl)-phenyl]urea, where $R^1$, $R^2$, $R^3$ and $R^4$ are each hydrogen, and $R^5$ is 4-methylphenyl, was prepared according to the following procedure: A 250 mL three-neck bottle was charged at room temperature with anthranoylanthranilic acid (0.05 mol) and 100 mL methyl ethyl ketone. Para-toluenesulfonyl isocyanate (0.05 mol) was then added, with stirring, and the reaction mixture was heated under reflux at about 80° C. for about 4 hours. Thereafter, the resulting suspension was cooled to about 40° C., and acetic anhydride (40 mL) was added. The resulting mixture was heated for an additional 3 hours. After cooling to about 10° C., the precipitate was filtered under suction, washed with acetone, and dried at about 50° C. under atmospheric pressure to produce a white powder in about 70% -85% yield. The Emission (fluorescence) maximum of the resultant powder was 526 nm. The excitation maximum is/was 380 nm. Differential Thermal Analysis showed the endothermic peak (melting point) at about 230° C. Intensity of fluorescence of the powder was 350 cd/m², as measured with a Minolta luminance meter under 365 nm excitation. Solubility of the powder in 2-butanone was less than 0.5% at room temperature.

EXAMPLE 2

Preparation of 1-(phenylsulfonyl)-3-[2-(4-oxo-4H-benzo[d]-[1,3]oxazine-2-yl)-phenyl]urea In accordance with the present disclosure, 1-(phenylsulfonyl)-3-[2-(4-oxo-4H-benzo[d]-[1,3]oxazine-2-yl)-phenyl]urea, where $R^1$, $R^2$, $R^3$ and $R^4$ are each hydrogen, and $R^5$ is phenyl, was prepared in the same manner as described in Example 1, above. Yields were between 70%-85%. The Emission (fluorescence) maximum of the resultant powder was 528 nm. The excitation maximum was 380 nm. Differential Thermal Analysis showed the endothermic peak (melting point) at about 222° C. Intensity of fluorescence of the powder was 320 cd/m², as measured with a Minolta luminance meter under 365 nm excitation. Solubility of the powder in 2-butanone was less than 0.5% at room temperature.

EXAMPLE 3

Preparation of 1-(2-methylphenylsulfonyl)-3-[2-(4-oxo-4H-benzo[d]-[1,3]oxazine-2-yl)-phenyl]urea In accordance with the present disclosure, 1-(2-methylphenylsulfonyl)-3-[2-(4-oxo-4H-benzo[d]-[1,3]oxazine-2-yl)-phenyl]urea, where $R^1$, $R^2$, $R^3$ and $R^4$ are each hydrogen, and $R^5$ is 2-methylphenyl, was prepared in the same manner as described in Example 1, above. Yields were between 70%-85%. The Emission (fluorescence) maximum of the resultant powder was 530 nm. The excitation maximum was 380 nm. Differential Thermal Analysis showed the endothermic peak (melting point) at about 207° C. Intensity of fluorescence of the powder was 260 cd/M², as measured with a Minolta luminance meter under 365 nm excitation. Solubility of the powder in 2-butanone was less than 1% at room temperature.

EXAMPLE 4

Preparation of 1-(4-chlorophenylsulfonyl)-3-[2-(4-oxo-4H-benzo[d]-[1,3]oxazine-2-yl)-phenyl]urea In accordance with the present disclosure, 1-(4-chlorophenylsulfonyl)-3-[2-(4-oxo-4H-benzo[d]-[1,3]oxazine-2-yl)-phenyl]urea, where $R^1$, $R^2$, $R^3$ and $R^4$ are each hydrogen, and $R^5$ is 4-chlorophenyl, was prepared in the same manner as described in Example 1, above. Yields were between 70%-85%. The Emission (fluorescence) maximum of the resultant powder was 539 nm. The excitation maximum was 380 nm. Differential Thermal Analysis shows the endothermic peak (melting point) at about 216° C. Intensity of fluorescence of the powder was 330 cd/m², as measured with a Minolta luminance meter under 365 nm excitation. Solubility of the powder in 2-butanone was less than 0.5% at room temperature.

The present disclosure has been described with particular reference to the preferred embodiments. It should be understood that variations and modifications thereof can be devised by those skilled in the art without departing from the spirit and scope of the present disclosure. Accordingly, the present disclosure embraces all such alternatives, modifications and variations that fall within the scope of the appended claims.

What is claimed is:
1. A benzoxazinone compound represented by the formula:

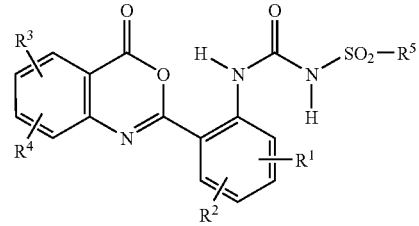

wherein:
each $R^1$, $R^2$, $R^3$, and $R^4$ is independently selected from the group consisting of: hydrogen, alkyl of 1-12 carbon atoms, substituted alkyl, aryl of 6-12 carbon atoms, substituted aryl, halo, and alkoxy; and
$R^5$ is selected from the group consisting of: alkyl of 1-12 carbon atoms, substituted alkyl, aryl of 6-12 carbon atoms, substituted aryl, halo, and alkoxy;
wherein each of said substituted alkyl and said substituted aryl groups have a substituent selected from the group consisting of: alkyl, aryl, halo, and alkoxy.

2. The benzoxazinone compound according to claim 1, wherein $R^1$, $R^2$, $R^3$, and $R^4$ are each hydrogen atoms.

3. The benzoxazinone compound according to claim 1, wherein $R^5$ is selected from the group consisting of phenyl, 2-methylphenyl, 4-methylphenyl, and 4-chlorophenyl.

4. The benzoxazinone compound according to claim 1, wherein said benzoxazinone is 1-(para-toluenesulfonyl)-3-[2-(4-oxo-4H-benzo[d][1,3]oxazine-2-yl)-phenyl]urea.

5. The benzoxazinone compound according to claim 1, wherein said benzoxazinone compound is nearly colorless.

6. The benzoxazinone compound according to claim 1, wherein said benzoxazinone compound fluoresces in a visible region.

7. The benzoxazinone compound according to claim 6, wherein said benzoxazinone compound fluoresces from about 520 nm to about 540 nm wavelength.

8. An article comprising the benzoxazinone compound according to claim 1, wherein said article is selected from the group consisting of ink, fluorescent ink, ink jet ink, colored paint, colorless paint, mass coloring polymer, film, coating, dispersion, data carrier, security marking, paper, spun fiber, dyed fiber, biochemistry tracer, and display.

9. An ink composition comprising:

a benzoxazinone compound represented by the formula:

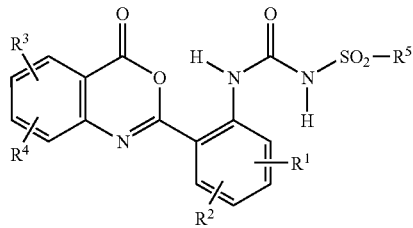

wherein each $R^1$, $R^2$, $R^3$, and $R^4$ is independently selected from the group consisting of: hydrogen, alkyl of 1-12 carbon atoms, substituted alkyl, aryl of 6-12 carbon atoms, substituted aryl, halo, and alkoxy; and $R^5$ is selected from the group consisting of: alkyl of 1-12 carbon atoms, substituted alkyl, aryl of 6-12 carbon atoms, substituted aryl, halo, and alkoxy; and wherein each of said substituted alkyl and said substituted aryl groups have a substituent selected from the group consisting of: alkyl, aryl, halo, and alkoxy; and at least one ink vehicle, wherein said ink vehicle comprises at least one solvent or water.

10. The ink composition according to claim 9, further comprising a surfactant.

11. The ink composition according to claim 9, wherein a benzoxazinone compound comprises about 0.001% to about 40.0% by weight of the total weight of the ink composition.

12. The ink composition according to claim 9, wherein said solvent is at least one selected from the group consisting of: an aliphatic alcohol solvent, ester, ketones, ethylene glycol monomethyl ether, ethylene glycol monoethyl ether, propylene glycol monomethylether, aliphatic polyols, 1,2-hexanediol, 2,4,6-hexanetriol, and combinations thereof.

13. The ink composition according to claim 9, further comprising a binder selected from the group consisting of: polyvinyl resins, polyvinyl alcohol, polyvinyl butyral, polyvinyl pyrrolidone, vinyl pyrrolidone-vinyl acetate copolymers; polyamine resins, polyallylamine, polyvinylamine, polyethyleneimine; polyacrylate resins, polymethyl acrylate, polyethylene acrylate, polymethyl methacrylate, polyvinyl methacrylate, amino resins, alkyd resins, epoxy resins, phenol resins, polyesterimide resins, polyamide resins, polyamideimide resins, silicone resins, phenol resins, ketone resins, rosin, rosin-modified resin phenols, maleic acid, fumaric acid resin, petroleum resins, cellulose resins, ethyl cellulose, nitrocellulose, natural resins, gum arabic, gelatin, and combinations thereof.

14. A mark comprising a benzoxazinone compound according to claim 1.

15. The mark according to claim 14, further comprising an article of commerce onto which said mark is printed, wherein said article of commerce is at least one selected from the group consisting of: currency, passports, chip cards, checks, check cards, credit cards, debit cards, identity cards, certificates, bank notes, and postal items.

16. A method for applying a mark according to claim 14 to an article comprising printing said mark on the article via a printing system, wherein said printing system is selected from the group consisting of: ink jet printing, thermal inkjet printing, piezo printing, dot matrix printing, laser printing, and combinations thereof.

* * * * *